United States Patent [19]

Bradford et al.

[11] Patent Number: Plant 7,193

[45] Date of Patent: Mar. 13, 1990

[54] NECTARINE TREE (RED GLEN)

[76] Inventors: Norman G. Bradford, 11875 E. Savana Rd.; Lowell G. Bradford, 12439 E. Savana Rd., both of Le Grand, Calif. 95333

[21] Appl. No.: 289,366

[22] Filed: Dec. 23, 1988

[51] Int. Cl.[4] ..... A01H 5/00

[52] U.S. Cl. ..... Plt./41

[58] Field of Search ..... Plt./41

[56] References Cited

U.S. PATENT DOCUMENTS

P.P. 5,666 2/1986 Bradford .

*Primary Examiner*—Robert E. Bagwill

[57] ABSTRACT

The present invention relates to a nectarine tree and more particularly to a new and distinct variety broadly characterized by a large size, vigorous, hardy, very productive and regular bearing tree. The fruit matures under the ecological conditions described approximately the last week in July, with first picking on July 28, 1988. The fruit is uniformly large in size, clingstone in type, very firm making excellent quality for keeping and shipping, very crisp in texture even after 3 weeks on the tree, full dark red in skin color, and acidic but sweet in flavor. The variety was developed as a hybridized seedling from the selected seed parent, Red Diamond (U.S. Plant Pat. No. 3,165), and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Red Glen". The present variety was hybridized in 1983 by us in a cultivated area of our experimental orchard at Bradford Farms near Le Grand, Calif. in Merced County (San Joaquin Valley). It was the result of a seedling using Red Diamond (U.S. Plant Pat. No. 3,165) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety most nearly resembles the fruit of Kism Grand (U.S. Plant Pat. No. 5,666) by being a clingstone nectarine, by ripening in late July, and by having excellent flavor, but is distinguished therefrom and an improvement thereon by having dark red skin color over the entire fruit surface, by being very much firmer for better storage life, and by having the ability to remain crisp on the tree for 3 weeks, which extends the harvesting and marketing period.

The present variety is similar to its selected seed parent, Red Diamond (U.S. Plant Pat. No. 3,165), in fruit appearance by being a full red colored nectarine with excellent firmness, but is distinguished therefrom by ripening 30 days later and by being a clingstone instead of a freestone.

DRAWING

The accompanying photograph shows the characteristics of the whole fruit in skin color and form, a characteristic fruit divided near its suture plane showing the flesh and pit cavity, a typical stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed while the fruit was hard, but eating ripe on Aug. 4, 1988. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Color.*—Dark grayish Brown [62. d.gy.Br].
- *Lenticels.*—Numerous. Color: Brownish orange [54. brO]. Size: ⅛ to ¼" [3.175 mm.–6.350 mm.].

Branches:
- *Size.*—Medium.
- *Texture.*—Medium.
- *Color.*—1st year wood — Topside: Grayish Red [19. gy.R]. 1st year wood — Underside: Brilliant yellow green [116. brill.YG]. Older wood: Dark grayish reddish brown [47. d.gy.rBr].
- *Lenticels.*—Numerous, very small.

Leaves:
- *Size.*—Large. Average length: 5¾" [146.1 mm.]. Average width: 1 5/16" [33.34 mm.].
- *Thickness.*—Medium.
- *Form.*—Elliptical.
- *Apex.*—Acuminate.

*Base.*—Acute.
*Surface.*—Smooth.
*Color.*—Dorsal surface: Deep yellow green [118. deep YG]. Ventral surface: Moderate yellow green [120. m.YG].
*Margin.*—Finely serrate.
*Venation.*—Pinnately net veined.
*Petiole.*—Average Length: ⅜" [9.525 mm.]. Average Thickness: 1/16" [1.588 mm.].
*Glands.*—Numbers: 2 to 8 per leaf. Position: Majority oppositely positioned on petiole and base of blade. Size: Medium. Form: Reniform. Color: Brilliant yellow green [116. brill.YG].
*Stipules.*—Numerous. Average length: ⅜" [9.525 mm.].

Flower buds:
*Hardiness.*—Hardy.
*Size.*—Medium.
*Length.*—Medium.
*Form.*—Free.
*Surface.*—Pubescent.

Flowers:
*Blooming period.*—Medium, as compared with other varieties.
*Size.*—Small.
*Color.*—Moderate pink [5. m.Pk].

FRUIT

Maturity when described: Hard but eating ripe, Aug. 4, 1988.
Date of first picking: July 28, 1988.
Date of last picking: Aug. 18, 1988.
Size: Uniform, medium.
*Average diameter axially.*—2¼" [57.15 mm.].
*Average traversely in suture plane.*—2⅝" [66.68 mm].
Form: Uniform, symmetrical, globose, but slightly compressed in the suture plane.
Longitudinal section form.—Oval.
Transverse section through diameter.—Round, with some slight compressing along suture.
Suture: An inconspicous line recessed into a slight depression extending from base to beyond apex and having a slight depression beyond pistil point.
Ventral surface: Rounded slightly.
Lips: Equal with more lipping toward the apex.
Cavity: Flaring, elongated in the suture plane, suture showing on one side.
Base: Slightly cuneate and somewhat truncate.
Apex: Slightly cuneate.
Pistil point: Apical, negligible in length, indented within the suture.
Stem:
*Size.*—Medium.
*Average length.*—⅜" [9.525 mm.].
*Average width.*—⅛" [3.175 mm.].
Skin:
*Thickness.*—Medium.
*Texture.*—Medium.
*Tenacity.*—Tenacious to flesh.
*Tendency to crack.*—None observed as of yet.
*Color.*—Very dark red [17. v.d.R] over a deep red [13. deep R] background.

Flesh:
*Color.*—Brilliant yellow [83. brill.Y] with some strong red [12. s.R] mottling next to the stone.
*Amygdalin.*—Scarce.
*Juice.*—Abundant, rich.
*Texture.*—Extremely firm, fine very crisp.
*Fibers.*—Abundant, fine, tender.
*Ripens.*—Evenly.
*Flavor.*—A tasteful blend of acid with an abundance of sugar.
*Aroma.*—Slight.
*Eating quality.*—Best.

STONE

Type: Clingstone.
Form: Oval.
Base: Straight.
Apex: Acute.
Sides: Equal.
Surface: Irregularly furrowed toward the ventral edge and pitted toward the base.
Ridges: Jagged toward the apex.
Color: Moderate brown [58. m.Br].
Pit wall: 3/16" [4.763 mm.] thick.
Tendency to split: Very slight.
Kernel:
*Form.*—Oval.
*Taste.*—Sweet.
*Viable.*—Yes.
*Average width.*—7/16" [11.11 mm.].
*Average length.*¾" [19.05 mm.].
Pellicle color: Moderate yellowish brown [77. m.yBr].
Amygdalin: Scant.

USE

Market: Fresh and long distance shipping.
Keeping quality: Best.
Shipping quality: Best.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which most nearly resembles the Kism Grand (U.S. Plant Pat. No. 5,666) nectarine variety by producing excellent flavored clingstone fruit that ripens in late July, but is distinguished from and an improvement on that variety by producing fruit that is dark red in skin color over the entire fruit surface, that is very much firmer for long distant shipping, and that remains crisp on the tree for 3 weeks, which will accommodate for a longer and more flexible harvesting period and also make tree ripened fruit more attainable.

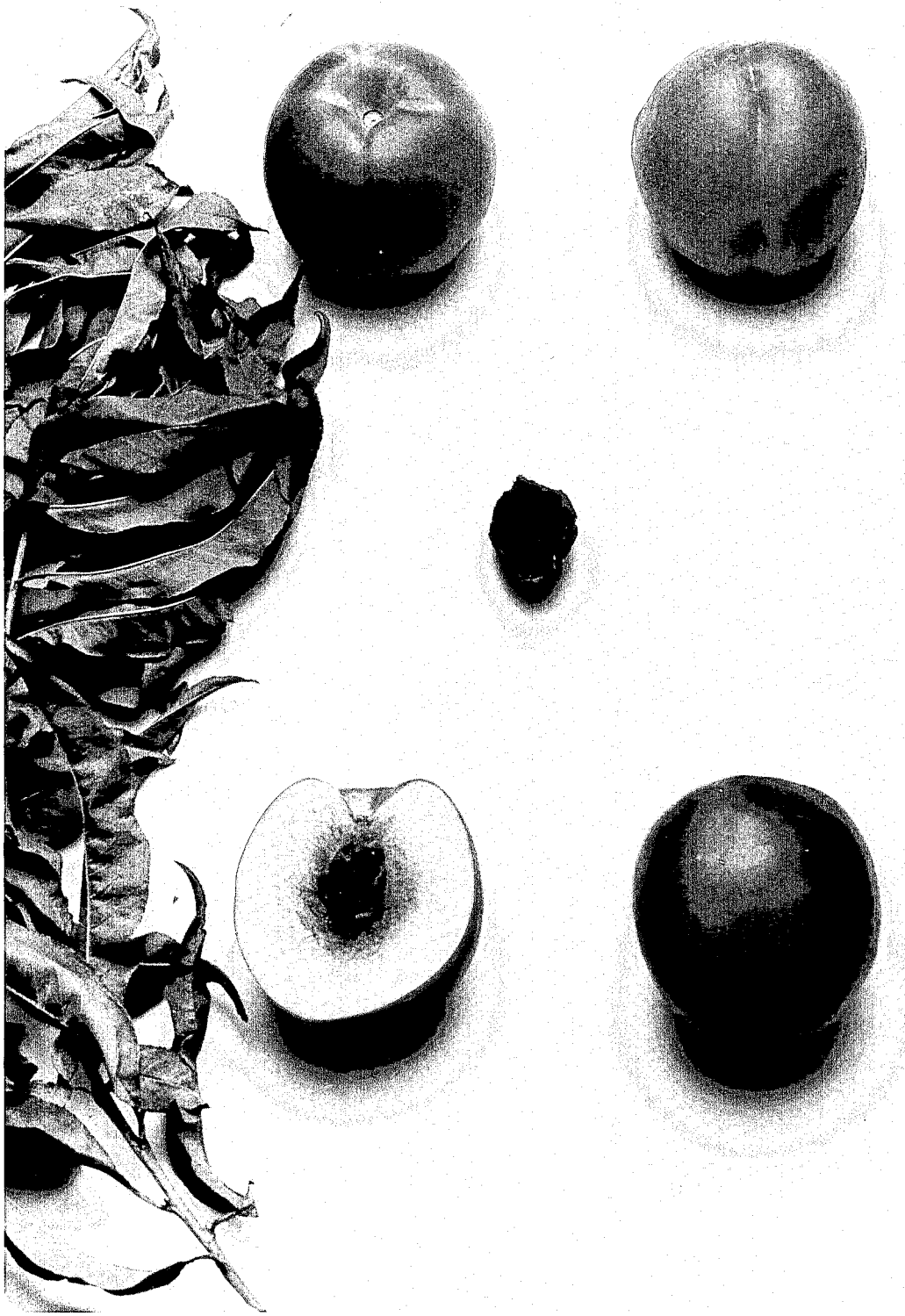

* * * * *